(12) United States Patent
Goldstein et al.

(10) Patent No.: US 8,267,083 B1
(45) Date of Patent: Sep. 18, 2012

(54) CONTINUOUS POSITIVE AIRWAY SUPPLY SYSTEM TO NASAL CANNULA HAVING SENSITIVE PRESSURE RELIEF VALVE

(75) Inventors: Mitchell Goldstein, Alta Loma, CA (US); Arnold M. Heyman, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 290 days.

(21) Appl. No.: 12/657,119

(22) Filed: Jan. 14, 2010

Related U.S. Application Data (63) Continuation-in-part of application No. 11/784,671, filed on Apr. 10, 2007, now Pat. No. 8,001,966.

(60) Provisional application No. 60/850,410, filed on Oct. 10, 2006.

(51) Int. Cl.
*A61M 11/00* (2006.01)

(52) U.S. Cl. .......... 128/204.18; 128/204.22; 128/204.26

(58) Field of Classification Search ............. 128/204.18, 128/204.21, 204.22, 204.26, 204.29; 137/557, 137/559; 116/276, 277, DIG. 7; 73/170.01, 73/170.05, 170.14, 37, 861.47
See application file for complete search history.

(56) References Cited

U.S. PATENT DOCUMENTS

| | | | | |
|---|---|---|---|---|
| 5,273,087 A | * | 12/1993 | Koch et al. ...................... | 141/94 |
| 6,116,273 A | * | 9/2000 | Tarr et al. ...................... | 137/539 |
| 6,202,684 B1 | * | 3/2001 | Angel et al. .................. | 137/557 |
| 6,237,624 B1 | * | 5/2001 | Neumair .................. | 137/505.41 |
| 8,001,966 B1 | * | 8/2011 | Goldstein et al. ........ | 128/204.18 |
| 2008/0115787 A1 | * | 5/2008 | Ingenito .................... | 128/205.13 |

* cited by examiner

*Primary Examiner* — Steven Douglas
(74) *Attorney, Agent, or Firm* — William W. Haefliger (57) ABSTRACT

The invention concerns a combination control for use in nasal cannula therapy, and includes a high flow, nasal cannula respiratory assistance ducted system, and a pressure relief valve having indicator structure, which typically includes a tubular body, a carrier slidable in the body, a plunger-indicator carried by the carrier, and a spring resisting carrier movement toward a cap on the body that defines an indicator window.

22 Claims, 8 Drawing Sheets

CONTINUOUS POSITIVE AIRWAY SUPPLY SYSTEM TO NASAL CANNULA HAVING SENSITIVE PRESSURE RELIEF VALVE

This application is a continuation-in-part of U.S. application Ser. No. 11/784,671, filed Apr. 10, 2007 now U.S. Pat. No. 8,001,966, which is a regular application converted from Provisional application Ser. No. 60/850,410, filed Oct. 10, 2006.

BACKGROUND OF THE INVENTION

This invention relates generally to nasal cannula therapy, and more particularly to improvements concerning fluid flow in nasal cannula therapy systems.

Nasal continuous positive airway pressure, NCPAP, is a used standard for administration of non-invasive positive airway pressure in the Neonate. Historically, Nasal Cannulae have been used at low flow rates (<1.5 1 pm) during infant weaning from assisted ventilation, or for maintenance in the sub-acute phase of chronic lung disease. Difficulty in regulation of pressure, and concerns regarding the damaging effects of inadequately warmed and humidified oxygen delivery systems on nasal mucosa, precluded the use of these devices in the more acute phases of respiratory distress and at the higher liter flow rates that would have been required to generate the pressures necessary to provide for that particular disease process. Certain devices held the promise of improved humidification and warming of the cannula flow, but introduced the possible deleterious effect of unknown pressure propagation as well as reported bacteria contamination of the circuit.

Accordingly, there was concern about delivering pressures that were excessive and possibly damaging to the respiratory tract, sinuses, ear drum or GI tract. Mechanical ventilators used for assisted respirator having built in features for monitoring flow and pressures and are excessively expensive to supply and operate.

SUMMARY OF THE INVENTION

It is a major object of the invention to provide solutions to the described problems and difficulties. Basically, the invention is embodied in a combination control including monitoring for use in nasal cannula therapy, that comprises:
  a) nasal cannula respiratory assistance ducted system,
  b) the system including the following ii) means and at least one or both of the following i) means and iii) means,
   i) flow metering first means associated with said system ducting, upstream of the nasal cannula,
   ii) safety pressure release and pressure level indicating second valve means also associated with said system ducting, downstream of the nasal cannula,
   iii) flow metering third means associated with the system ducting, and downstream of the pop-off valve.
Another object of the invention includes provision, and in series sequence, of:
  i) an oxygen gas source,
  ii) means receiving oxygen from said source, and air, for blending air, oxygen, and/or nitric oxide, in an output stream,
  iii) a heater/humidifier to heat and humidify said stream,
  iv) a nasal cannula to receive the heated and humidified stream, for administration to the infant or patient,
  v) said i), ii) and iii) means as defined.
A further object includes provision of a by-pass outlet from the system for flow to the patient, downstream of said first means.

Yet another object includes provision of a proportioning valve or other valve extending at a system outlet, and operating as said second means.

Another object of the present invention is to provide for requisite warmth and humidification of the air stream. The complications of inadvertent pressure propagation are avoided. The device allows for demand flow without using a conventional ventilator and subsequent costs.

Further objects include provision of
  $x_1$) a tubular body having an end opening, and a step shoulder located in said body,
  $x_2$) a pressure responsive carrier receive in and movable axially in the body, away from said step shoulder,
  $x_3$) a plunger carried by the carrier, and having a stem extending axially toward the end opening,
  $x_4$) a spring in the body acting to resist carrier axial displacement toward the end opening that would displace the plunger stem axially,
  $x_5$) a cap on the body having at least one window via which axial displacement of the stem is visually observable.

These and other objects and advantages of the invention, as well as the details of an illustrative embodiment, will be more fully understood from the following specification and drawings, in which:

DETAILED DESCRIPTION

Figure 1:
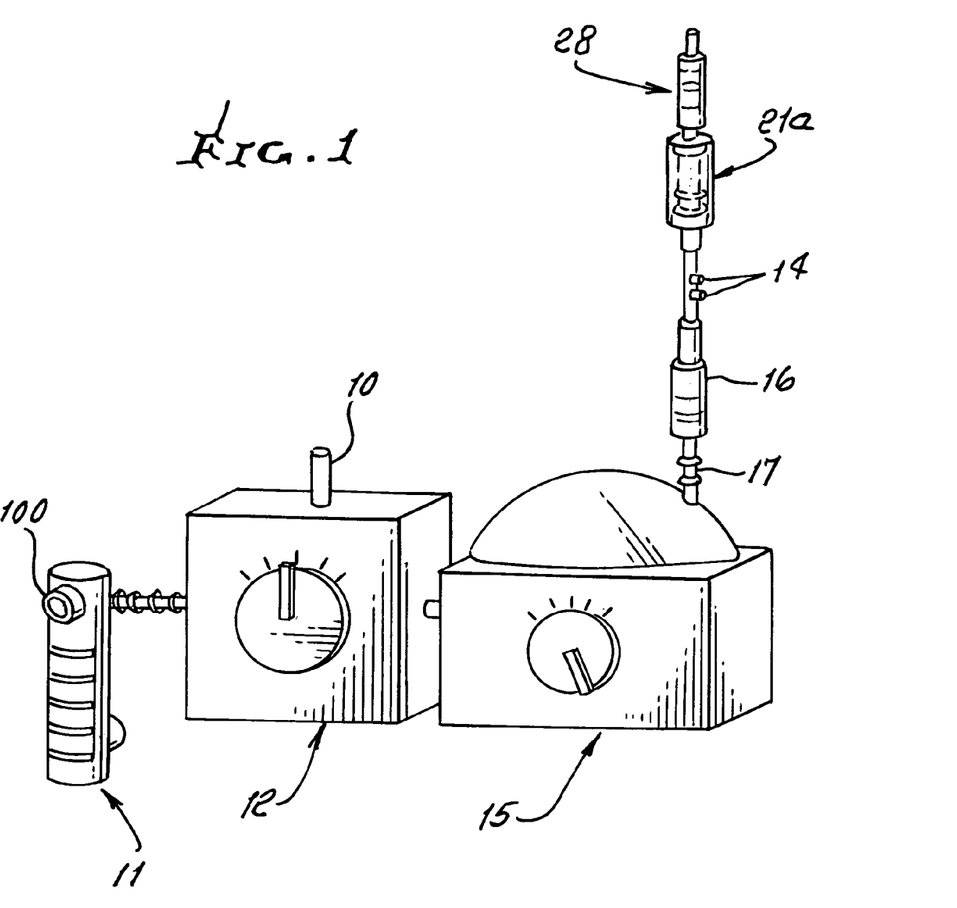
FIG. 1 is a system diagram.

Referring first to FIG. 1, showing a preferred system, air supplied at 10, and oxygen supplied at 100 enter a blending zone 12, to be thoroughly mixed or blended. A control 11 to increase or decrease flows from the oxygen supply 100 is shown. The flowing mix passes to a flow meter at 16 via a warmer/humidifier 15, which may consist of warm water into which the flow is injected to bubble up and continue flowing as at 17, as warmed, humidified air/oxygen blend. Some of the flow passes to the small tubes or prongs 14 for supply to the infant's lungs. Some of that supply may variably leak to atmosphere, via the nostrils or expelled via the infant's mouth, for example along with flow expelled from the lungs, during breathing. Flow pressure supplied to the cannula is desirably below about 10 cm water pressure. The oxygen supply, as at hospital wall outlet 100, is typically about 50 psi (3,154, cm/H$_2$0).

Figure 4:
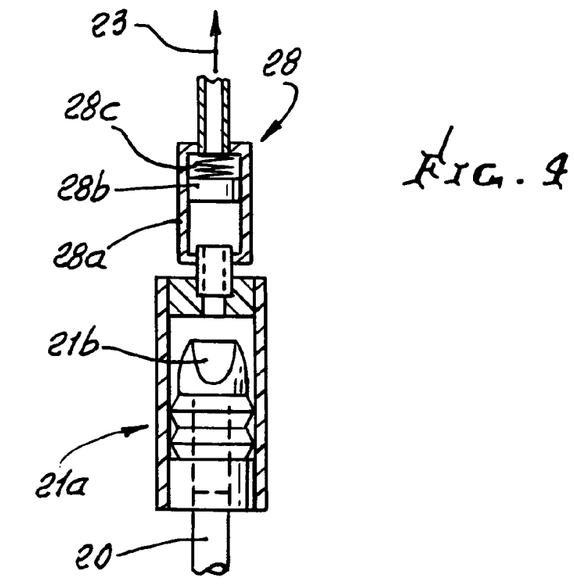
FIG. 4 is a section taken through a pressure relief flutter type valve, in a system.

Remnant air passes in duct 20 FIG. 4 to an outlet, such as a "pop-off" valve. The latter preferably takes the form of a proportioning valve, seen at 21*a* in FIG. 4, and having elastomeric flow control sections 21*b* that excessive air pressure forcibly spread apart, for example to suddenly discharge the flow when the pressure exceeds about 10 cm water pressure. See also arrow 23, indicating discharge to atmosphere. Need for means to maintain pressure in the duct at or near 10 cm of water derives from the infant's lungs, which should not be subjected to excessive pressure. Such excessive pressure could arise as from closing of the infant's mouth or covering of its nostrils, or both, excessive pressure being variably transmitted to 21*a*. Proportioning valve 21 or 21*a* is herein designated at times as a form of pressure relief "second means".

Figure 5:
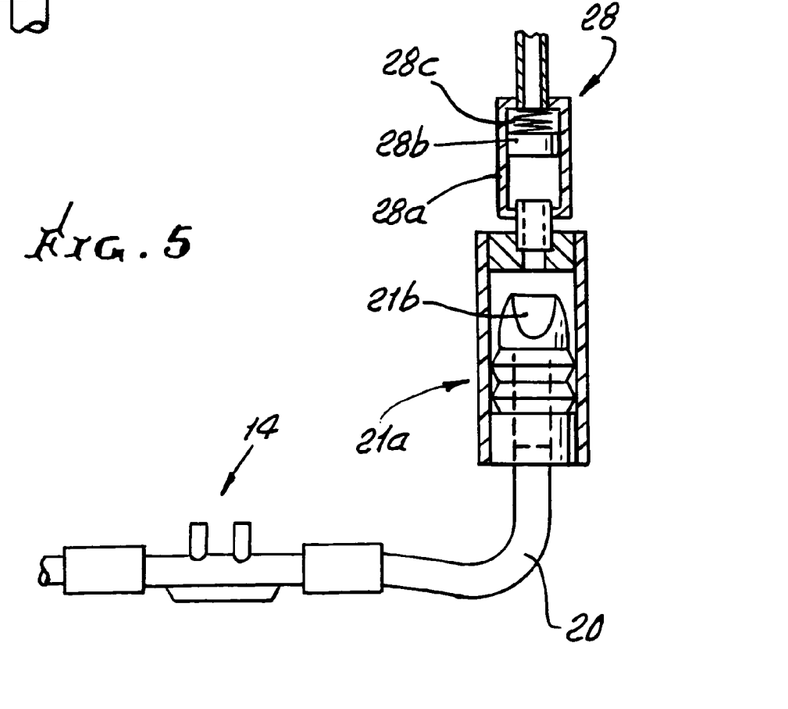
FIG. 5 is a view showing system ducting, a pressure relief valve in series in the ducting; and a flow meter downstream of the pressure relief valve.
Figure 6:
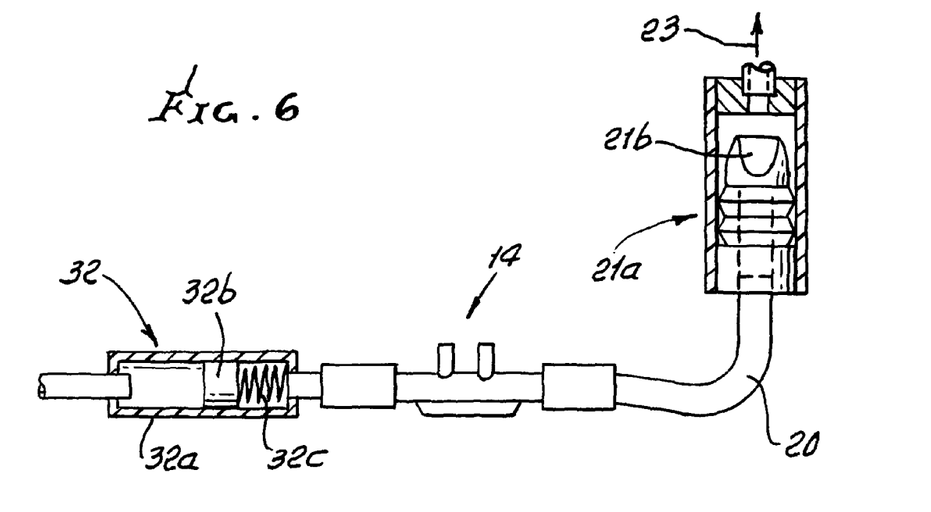
FIG. 6 is a view showing system ducting, a pressure relief valve in series in the ducting, and a flow meter upstream of cannula in the ducting.
Figure 7:
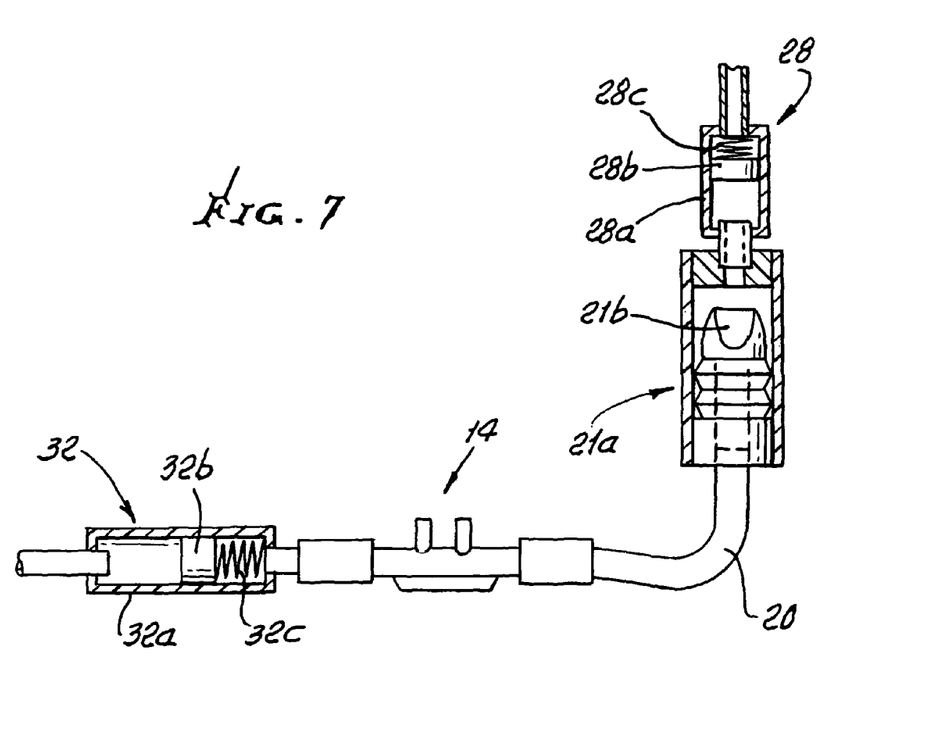
FIG. 7 is a view like FIG. 6, but also showing an additional flow meter downstream of the pressure relief valve.

The invention also contemplates provision and operating of flow metering third means, indicated at 28 in FIGS. 1 and 5, downstream of the cannula 14, and downstream of the second means 21*a*; and/or provision and operation of flow metering first means, indicated at 32 in FIG. 6, in the ducting upstream of the nasal cannula 14. FIG. 7 shows use of both 28 and 32 in the system ducting. These elements typically have visible flow rate readouts, at the sides of transparent tubing 28*a* and 32*a*, containing pistons 28*b* and 32*b* which shift position lengthwise in the tubing, as flow rates vary, to indicate such rates. Air flow pressure pushes such pistons against compression springs 28*c* and 32*c*. If indicated flow at 28 shows loss of flow at 14, the flow at 11 can be adjusted to compensate for the loss to atmosphere at 21*a*, consistent with the infant's or patient's lungs. Such indicated rates, prior to adjustment, could for example be too low as a result of excessive leaking at the infant's nostrils or mouth.

Figure 3:
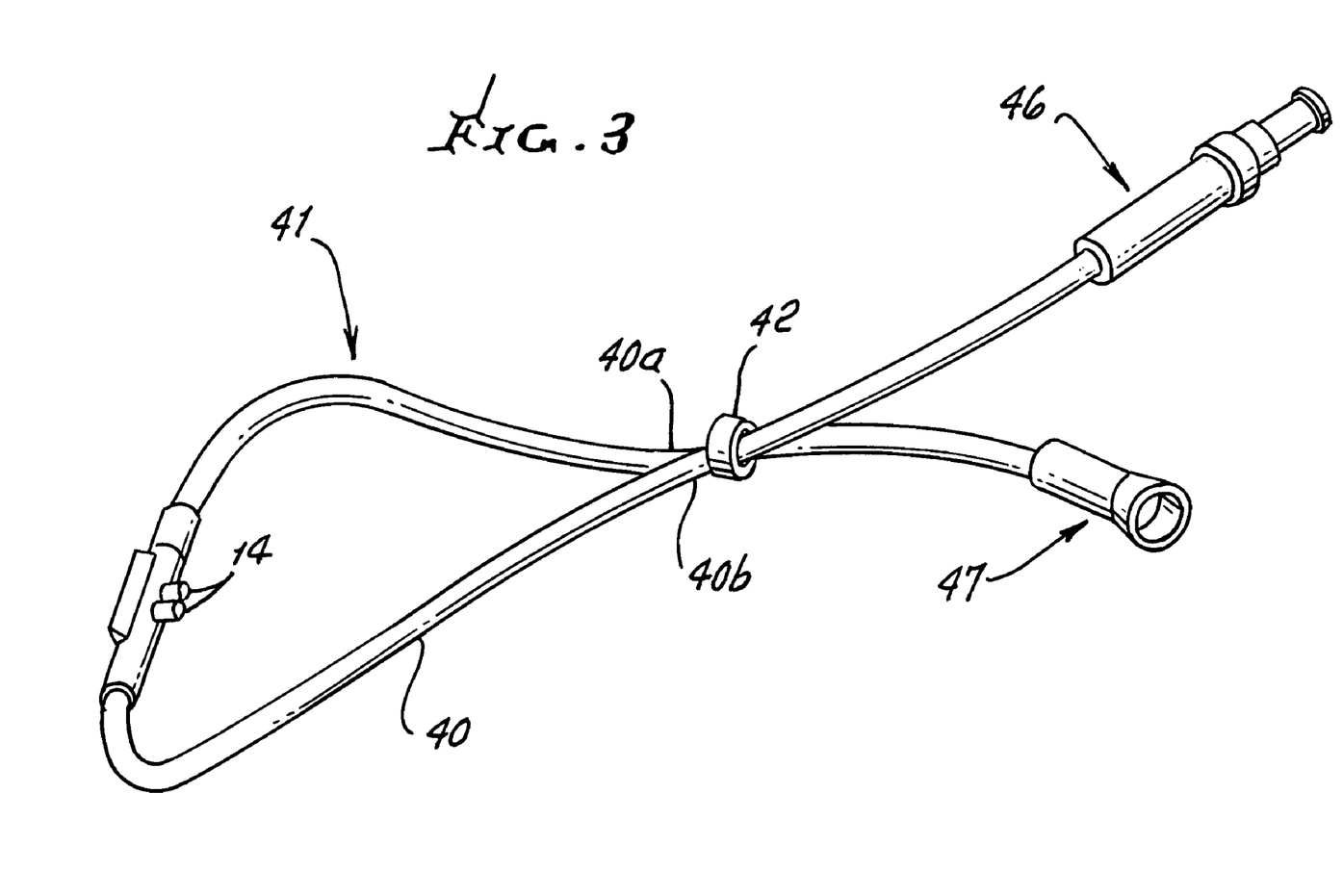
FIG. 3 is a perspective view showing actual elements of the system.

FIG. 3 shows the ducting to include plastic tubing 40 forming a loop 41, as a result of optional clasp 42 loosely grasping tubing portions 40*a* and 40*b* permitting relative slippage to contract or enlarge the loop, around the infant's head, for holding cannula prongs 14 in the nostrils. Note inclusion of the proportioning valve enclosure 46, in series with the tubing. Fixture 47 connects the tubing to system ducting downstream of the heater humidifier 15.

Figure 2:
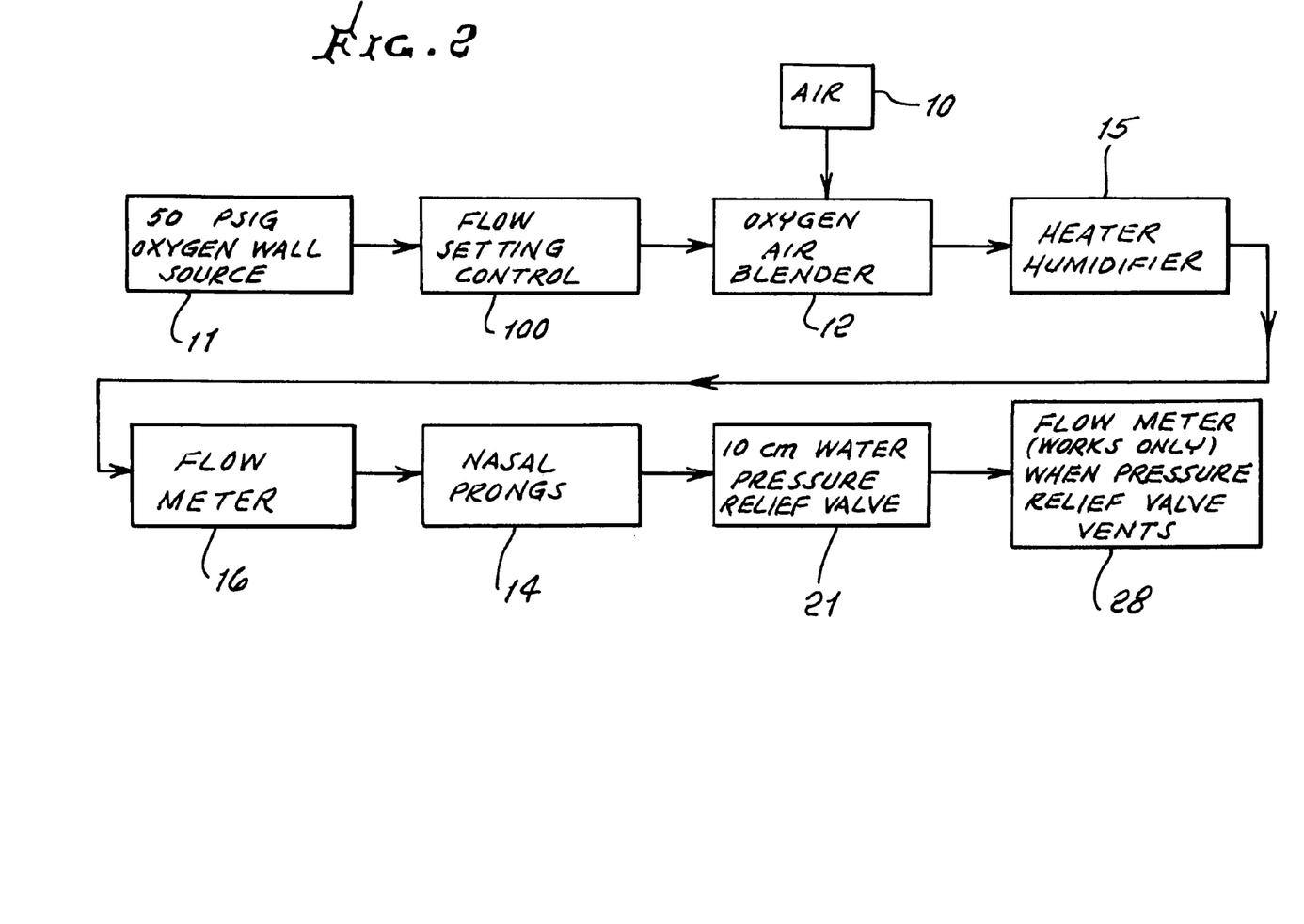
FIG. 2 is a system block diagram.

FIG. 2 is a block diagram of the system.

Referring now to the preferred valve of FIGS. 8-15, the following pressure indicating and pressure relief elements are shown, these being an improvement upon and substitute for the FIG. 4 valve:

$x_1$) a tubular body 100 having an end opening 101, and a step shoulder 102, located in said body, $x_2$) a pressure responsive carrier 103 received in and movable axially in that body, away from the step shoulder, $x_3$) a plunger 104 carried by the carrier, and having a stem 104*b* extending axially toward said end opening, $x_4$) a helically wound spring 106 in the body acting to resist carrier axial displacement toward said end opening that would displace the plunger stem axially, $x_5$) a cap 107 on the body having at least one window 108 via which axial displacement of the stem is visually observable, due to excess air pressure exertion.

The following features are also of importance as to reliability, simplicity, and unusually effective operation.

Figure 8:
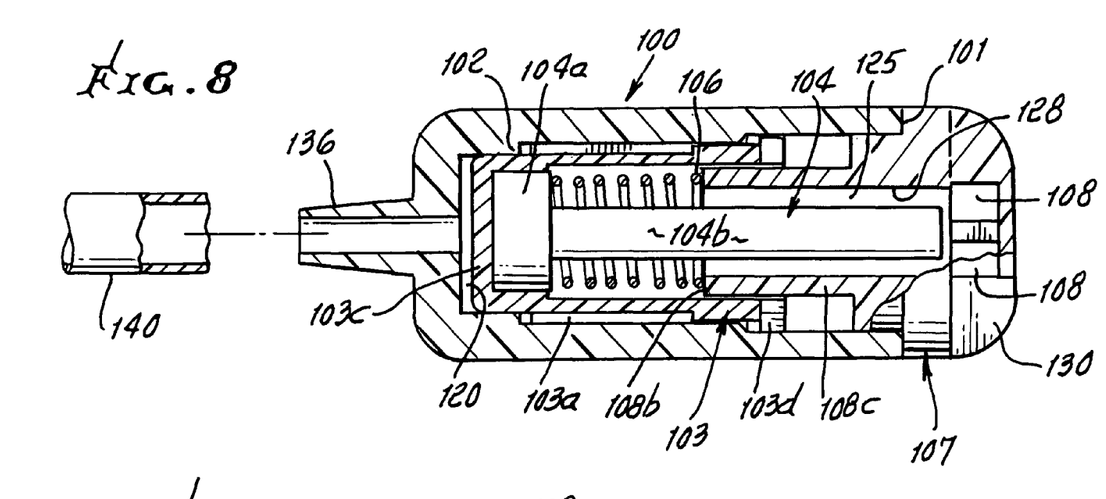
FIG. 8 is a section taken through a pressure relief-indication valve.
Figure 9:
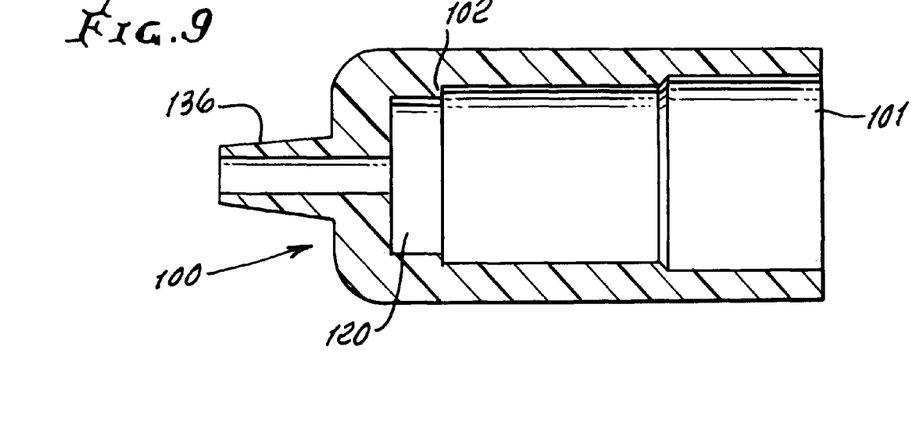
FIG. 9 is a section taken through a valve housing.
Figure 12:
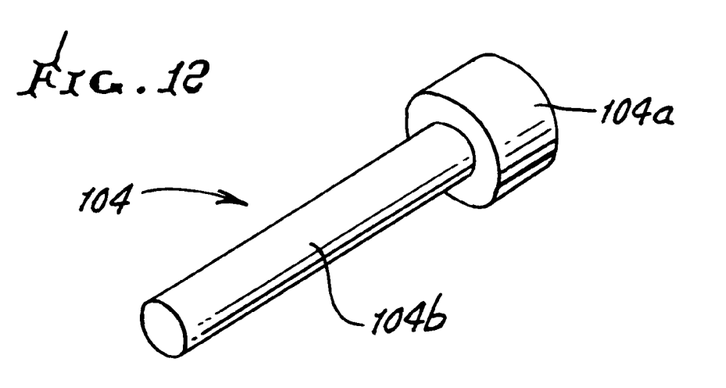
FIG. 12 is a perspective view of an indicator plunger movable endwise in the housing and cap.
Figure 13:
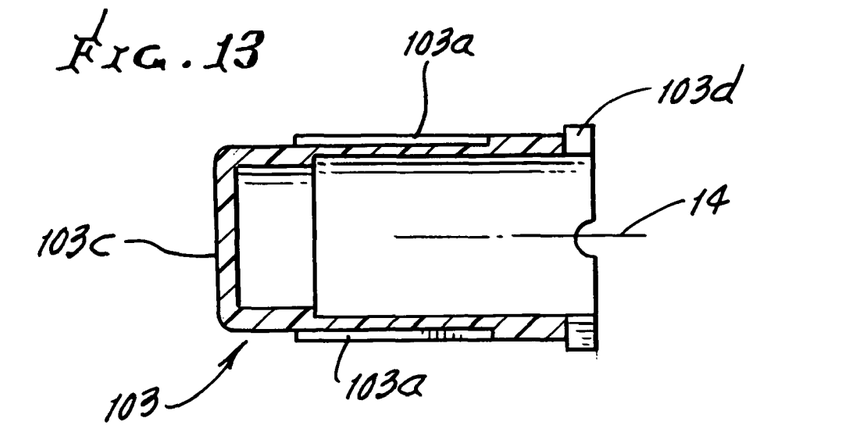
FIG. 13 is a section taken through a plunger carrier.
Figure 14:
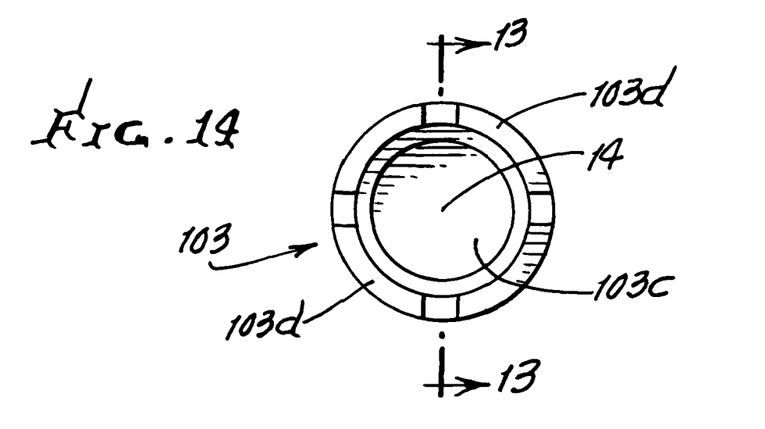
FIG. 14 is an end view of the carrier.
Figure 15:
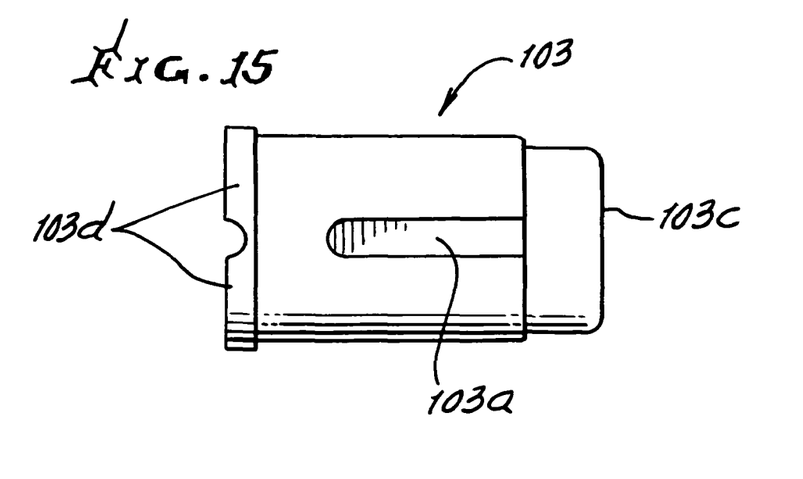
FIG. 15 is a side elevation view of the carrier.

Plunger 104 has a head 104*a* and a stem 104*b*, received by and endwise assembled to the tubular carrier 103, to be positioned by the carrier relative to the window 108, for visibly indicating pressure "pop-off" or relief, even though such relief may not be audibly detectable due to very low pressure level. Ducting 103*a* on the carrier exterior passes pressurized flow toward window 108, for exhausting via clearances to the exterior, after spring force is overcome by air pressure exerted against the closed end 103*c* of the carrier, via chamber 120.

Also, the carrier has multiple speed peripheral guides 103*d* that protrude radially outwardly to easily slide against cylindrical bore 100*a* of the body 100, during piston movement of the carrier with pressure exertion against carrier closed end 103*c*. Guides 103*d* are annularly spaced apart, circularly about axis 14, to allow flow of air past the carrier and via clearances to the escape window or windows 108, as via clearance at 125 between the stem or shaft 104*b* of the plunger and the cylindrical bore 128 of the cap 107.

Figure 10:
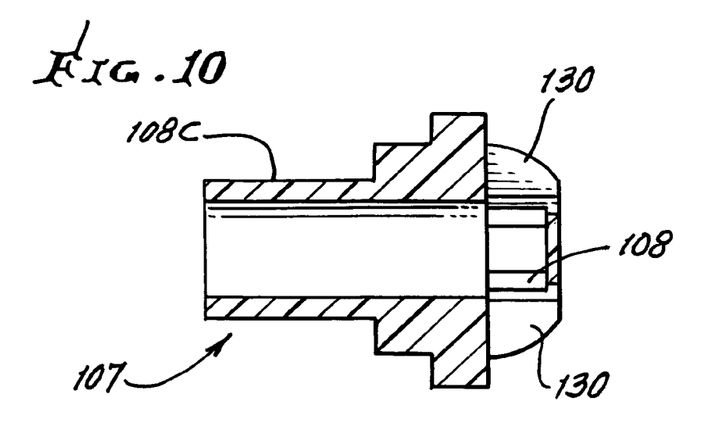
FIG. 10 is a section taken through an end cap that fits on the valve housing, for indicator view purposes.

Note that light weight, sensitive spring 106 is endwise compressed between plunger head 104*a* and the end shoulder 108*b* of a tubular stem 108*c* of the cap. That stem also assists centered guidance of travel of the carrier.

Figure 11:
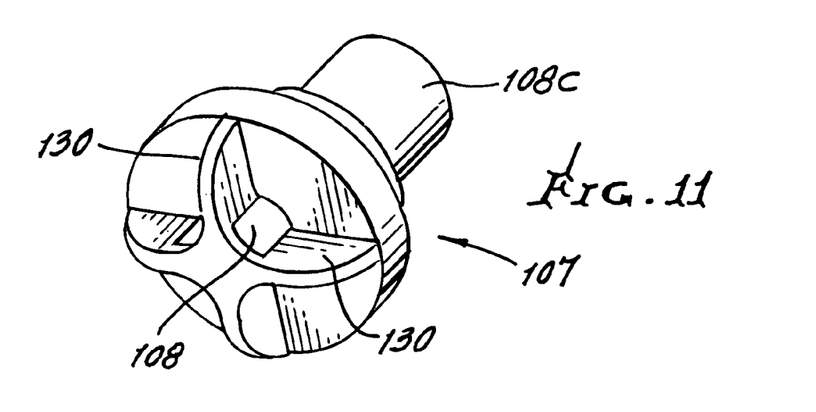
FIG. 11 is a perspective view of the FIG. 10 end cap.

Ribbing 130 on the cap 107 extends laterally of the window or windows 108, and protects the indicating end 104*c* of the plunger stem 104*b* as the stem is displaced into lateral alignment with the window.

Finally, it will be noted that the carrier and body form pressure receiving chamber 120 in communication with a tubular endwise projection 136 from the body, to receive air pressure exerted on the carrier via cannular tubing 140 fitting on 136.

We claim:

1. An air pressure relief and pressure level indicating valve unit, connected with a nasal cannula duct, comprising in combination $x_1$) a tubular body having an end opening, and a step shoulder located in said body, $x_2$) a pressure responsive carrier receive in and movable axially in said body, away from said step shoulder, $x_3$) a plunger carried by the carrier, and having a stem extending axially toward said end opening, $x_4$) a spring in the body acting to resist axial displacement of said carrier toward said end opening that would displace the plunger stem axially, $x_5$) a cap on the body having at least one window via which axial displacement of the stem due to excess air pressure exertion is visually observable.

2. The combination of claim 1 wherein said plunger has a head received and positioned by the carrier.

3. The combination of claim 1 including ducting on the carrier to pass pressurized air to flow toward the window after the carrier moves axially away from said step shoulder.

4. The combination of claim 3 wherein the carrier has peripheral guides that guide slidable movement of the carrier, and which are annularly spaced apart to pass escape flow of pressurized air after the carrier moves away from said step shoulder.

5. The combination of claim 1 including protective ribbing on the cap extending laterally of said window or windows.

6. The combination of claim 2 wherein the spring is a helically wound spring endwise confined between said head and a shoulder defined by the cap.

7. The combination of claim 1 including a tubular projection carried by the body, and nasal cannula tubing connected with said projection.

8. The combination of claim 7 wherein the carrier and body form a pressure receiving chamber in communication with said projection 1 to receive air pressure exerted on the carrier.

9. A combination control for use in nasal cannula therapy, comprising a) a high flow, nasal cannula respiratory assistance ducted system,
b) the system including:
   i) flow metering first structure upstream of the nasal cannula,
   i) second structure including a proportioning valve also associated with said system ducting, serving as a safety release valve, downstream of the nasal cannula,
   ii) flow metering third structure associated with the system ducting, and downstream of the nasal cannula,
c) said second structure comprising
   $x_1$) a tubular body having an end opening, and a step shoulder located in said body,
   $x_2$) a pressure responsive carrier received in and movable axially in said body, away from said step shoulder,
   $x_3$) a plunger carried by the carrier, and having a stem extending axially toward said end opening,
   $x_4$) a spring in the body acting to resist carrier axial displacement of said carrier toward said end opening that would displace the plunger stem axially,
   $x_5$) a cap on the body having at least one window via which axial displacement of the stem is visually observable.

10. The combination of claim 9 and including, in series sequence
   i) an oxygen gas source,
   ii) blending structure receiving oxygen from said source, and air, for blending air and oxygen and/or nitric oxide forming an output stream,
   iii) a heater/humidifier to heat and humidify said output stream,
   iv) said nasal cannula to receive the heated and humidified stream.

11. The combination of claim 9 wherein said nasal cannula comprises a by-pass outlet from the system ducting for air and oxygen flow to the patient's nose, downstream of said first structure.

12. The combination of claim 10 wherein said nasal cannula comprises a by-pass outlet from the system ducting for air and oxygen flow to the patient's nose, downstream of said first structure.

13. The combination of claim 11 wherein said proportioning valve structure is positioned for discharging excessive-pressure air and oxygen blend from said ducting.

14. The combination of claim 11 wherein said ducting includes plastic tubing forming a loop, said bypass outlet projecting from the loop, and a holder optionally clasping two portions of the tubing to form the loop.

15. The combination of claim 9 wherein said included flow metering first or third structure comprises a flow metering element in a ducting system.

16. The combination of claim 9 wherein said included flow metering first and third structure comprises flow metering elements in spaced apart sections of the ducting.

17. The combination of claim 9 wherein said first structure is located upstream of said second structure.

18. The method of controlling air/oxygen flow to a nasal cannula, the method comprising a step of controlling air/oxygen flow with a control including
   a flow, nasal cannula respiratory assistance ducted system,
   a flow metering primary means associated with said system ducting, and
   a safety pressure release valve second means also associated with said system ducting,
   said second means including a tubular body, a carrier slidable in the body, a plunger-indicator carried by the carrier, and a spring resisting carrier movement toward a cap on the body that defines an indicator window.

19. The method of claim 18 including providing an outlet for flow to a patient upstream of said flow metering primary means and second means.

20. The method of claim 18 which includes providing, in series sequence:
   i) an oxygen gas source,
   ii) means receiving oxygen from said source, and air, for blending air, oxygen and/or nitric oxide forming an output stream,
   iii) a heater/humidifier to heat and humidify said output stream,
   iv) a nasal cannula to receive the heated and humidified stream,
   v) flow metering primary means, and
   vi) said safety pressure release secondary valve means.

21. The method of claim 18 which includes providing a by-pass outlet from the system for flow to the patient, downstream of said first means.

22. The method of claim 19 including providing a by-pass outlet from the system for flow to the patient, downstream of said first and upstream of the second means.

\* \* \* \* \*